United States Patent [19]

Artz et al.

[11] Patent Number: 4,684,744
[45] Date of Patent: Aug. 4, 1987

[54] STILBENE DERIVATIVES

[75] Inventors: Klaus Artz, Muttenz; Hans R. Meyer, Binningen, both of Switzerland; Dieter Reinehr, Kandern, Fed. Rep. of Germany; Kurt Weber, Basel, Switzerland

[73] Assignee: Ciga-Geiby Corporation, Ardsley, N.Y.

[21] Appl. No.: 714,250

[22] Filed: Mar. 21, 1985

[30] Foreign Application Priority Data

Mar. 27, 1984 [CH] Switzerland .......................... 1526/84

[51] Int. Cl.$^4$ .................. C07C 121/66; C07C 69/616
[52] U.S. Cl. ..................... 558/388; 558/404; 558/406; 560/11; 560/41; 560/81; 562/429; 562/449; 562/488; 564/156; 568/34; 570/184
[58] Field of Search .............. 260/465 G; 560/81, 11, 560/41; 562/488, 429, 449; 568/34; 564/156; 570/184; 558/388, 404, 406

[56] References Cited

U.S. PATENT DOCUMENTS

| | | | |
|---|---|---|---|
| 4,108,887 | 8/1978 | Fleck et al. | 260/465 H |
| 4,145,362 | 3/1979 | Brepoels et al. | 260/465 G |
| 4,196,229 | 4/1980 | Fleck et al. | 427/158 |
| 4,440,694 | 4/1984 | Bellus et al. | 260/465 D |

FOREIGN PATENT DOCUMENTS 475184 8/1969 Fed. Rep. of Germany .
1465661 2/1977 United Kingdom .

*Primary Examiner*—Dolph H. Torrence
*Attorney, Agent, or Firm*—Edward McC. Roberts; Kevin T. Mansfield; Irving M. Fishman

[57] ABSTRACT

Stilbene derivatives of the formula

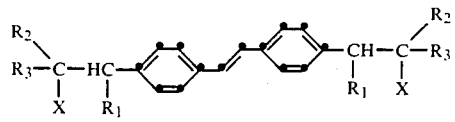

wherein X is chlorine or bromine, $R_1$ is hydrogen, carboxyl, cyano, $C_1$–$C_6$-alkyl or a non-chromophorically esterified carboxyl group, and $R_2$ and $R_3$ independently of one another are each hydrogen, unsubstituted or non-chromophorically substituted $C_1$–$C_6$-alkyl or $C_3$–$C_4$-alkenyl, or a non-chromophoric substituent of the 2nd order.

They are valuable intermediates for producing optical brighteners of the 4,4'-disubstituted stilbene series.

5 Claims, No Drawings

STILBENE DERIVATIVES

The present invention relates to novel stilbene derivatives, to a process for producing them, and to their use as intermediates for the production of optical brighteners of the 4,4'-disubstituted stilbene series.

From the German Auslegeschrift No. DE-A-2,602,750, it is known that 4,4'-divinylstilbenes can be produced from substituted styrenes, divinylbenzoins, stilbenes which carry in each of the 4- and 4'-positions an activated, unsubstituted or substituted methylene group or a reactive carbonyl group or a functional derivative thereof, or from fumaric acid-di-(p-vinylphenoxy) esters. The compounds used as starting materials for this purpose are difficult to obtain (for example the aldehydes), or the chosen syntheses are very complicated. The method of producing 4,4'-divinylstilbenes from stilbene-4,4'-dicarboxylic acid chloride and an olefin, with the addition of a palladium catalyst, is known from the European Patent Application No. EP-A 0,040,581. The stilbene-4,4'-dicarboxylic acid chloride usable as starting material is obtained from stilbene-4,4'-dicarboxylic acid, which is difficult to produce.

There have now been found novel starting materials for producing optical brighteners of the 4,4'-divinylstilbene series, which starting materials are readily obtainable.

The stilbene derivatives according to the invention correspond to the formula

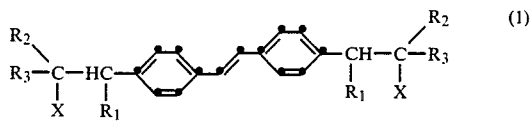

(1)

wherein
X is chlorine or bromine,
$R_1$ is hydrogen, carboxyl, cyano, $C_1$–$C_6$-alkyl or a non-chromophorically esterified carboxyl group, and
$R_2$ and $R_3$ independently of one another are each hydrogen, unsubstituted or non-chromophorically substituted $C_1$–$C_6$-alkyl or $C_3$–$C_4$-alkenyl, or a non-chromophoric substituent of the 2 nd order.

$C_1$–$C_6$-alkyl groups can be straight-chain or branched-chain. Those having 1–4, and especially 1 or 2, C atoms are preferred. $C_3$–$C_4$-alkenyl groups preferably contain 3 C atoms. The following may be mentioned as examples of such alkyl and alkenyl groups: the methyl, ethyl, n-propyl, isopropyl, butyl, sec-butyl, tert-butyl, n-pentyl, n-hexyl, allyl and butenyl groups.

Suitable as non-chromophoric substituents on alkyl or alkenyl groups as defined are for example: alkoxy, hydroxyalkoxy or alkoxycarbonyl groups. Alkoxy moieties in the substituents mentioned preferably contain 1 to 6, and particularly 1 or 2, C atoms.

Non-chromophoric substituents of the 2nd order are electron-attracting substituents which impart no colour to the compounds of the formula (1), which would be detrimental to their use for producing optical brighteners. Examples which may be mentioned are: the cyano group, the carbonamide group, the carboxyl group, carboxylic acid ester groups and sulfonyl groups. Non-chromophorically esterified carboxyl groups are for example carboxylic acid alkyl ester or carboxylic acid alkenyl ester groups, wherein the alkyl or alkenyl, as mentioned above, can be substituted. Carboxylic acid ester groups are preferably carboxylic acid alkyl ester groups, wherein the alkyl can be substituted by hydroxyl or by alkoxy, alkoxyalkoxy or hydroxyalkoxy groups of the type mentioned above. Sulfonyl groups are preferably alkyl-, phenyl- or benzyl sulfonyl groups, wherein the alkyl can be substituted by alkoxy or alkoxyalkoxy groups of the type mentioned above.

Preferred stilbene derivatives of the formula (1) are those
wherein
$R_1$ is hydrogen, $C_1$–$C_4$-alkyl or COOR, in which R is $C_1$–$C_4$-alkyl or $C_3$–$C_4$-alkenyl,
$R_2$ is hydrogen, $C_1$–$C_4$-alkyl, $C_1$–$C_4$-alkyl substituted by $C_1$–$C_4$-alkoxy or $C_1$–$C_4$-alkoxycarbonyl, or is $C_3$–$C_4$-alkenyl, cyano, —$COOR_o$, in which $R_o$ is hydrogen, $C_1$–$C_4$-alkyl, hydroxy-$C_2$–$C_4$-alkyl, $C_1$–$C_4$-alkoxy-$C_2$–$C_4$-alkyl, $C_1$–$C_4$-alkoxy-$C_2$–$C_6$-alkoxy-$C_2$–$C_4$-alkyl or $C_2$–$C_6$-hydroxyalkoxy-$C_2$–$C_4$-alkyl, or $SO_2R_x$, in which $R_x$ is $C_1$–$C_4$-alkyl, $C_1$–$C_4$-alkoxy-$C_2$–$C_4$-alkyl, $C_1$–$C_4$-alkoxy-$C_2$–$C_4$-alkoxy-$C_2$–$C_4$-alkyl, phenyl or benzyl, and is hydrogen, $C_1$–$C_4$-alkyl, or $C_1$–$C_4$-alkyl substituted by $C_1$–$C_4$-alkoxy or $C_1$–$C_4$-alkoxycarbonyl.

Also preferred are stilbene derivatives of the formula (1)
wherein
X is chlorine,
$R_1$ is hydrogen or $C_1$–$C_2$-alkyl,
$R_2$ is $C_3$–$C_4$-alkenyl, cyano, or —$COOR_o$ or —$SO_2R_x$, in which $R_o$ is hydrogen or $C_1$–$C_4$-alkyl and $R_x$ is $C_1$–$C_4$-alkyl, and
$R_3$ is hydrogen or $C_1$–$C_4$-alkyl.

Particularly preferred are stilbene derivatives of the formula (1) wherein
$R_1$ is hydrogen,
$R_2$ is cyano, or —$COOR_o$ or —$SO_2R_x$, in which $R_o$ is hydrogen, methyl or ethyl, and $R_x$ is methyl or ethyl, and
$R_3$ is hydrogen;
as well as the stilbene derivative of the formula (1) wherein $R_1$ and $R_3$ are hydrogen, and $R_2$ is cyano.

The stilbene derivatives of the formula (1) can be produced, in a manner known per se, by reacting 1 mol of a bis-diazonium compound of the formula

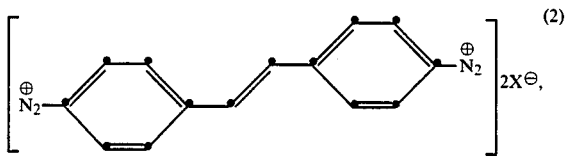

(2)

wherein X is chlorine or bromine, with 2–8, preferably 3–6, mols of a compound of the formula

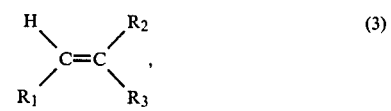

(3)

wherein $R_1$, $R_2$ and $R_3$ have the meanings defined in the foregoing, in the presence of a substance containing copper, as a catalyst, for example copper powder, copper oxide or copper salts, or mixtures thereof, in a solvent miscible with water.

The catalyst used is preferably a copper (I) halide, particularly copper(I) chloride.

The reaction is performed at a pH-value of 1-5, preferably 1-2.

Suitable water-miscible solvents are for example: acetone, methyl ethyl ketone, acetonitrile, N-methylpyrrolidone, $C_1$-$C_4$-alkanols, dimethylformamide and acetic acid. The reaction can also be performed in water, without the addition of further solvents.

The temperature at which the reaction is carried out is between $-10°$ and $+50°$ C. The preferred temperature range is between $0°$ and $30°$ C.

Compounds of the formula (1) wherein $R_2$ is cyano or —$COOR_o$ can be produced also by exchange of one of these substituents for another. Thus carboxylic acid esters are obtained from the corresponding nitriles, by known methods, by way of the imino ethers (cf. Houben-Weyl, Vol. 8, p. 536), or by acid-catalysed esterification or transesterification (cf. Houben-Weyl, Vol. 8, pp. 516, 528). The carboxylic acids are obtained by acid saponification of the nitriles or carboxylic acid esters (cf. Houben-Weyl, Vol. 8, p. 418).

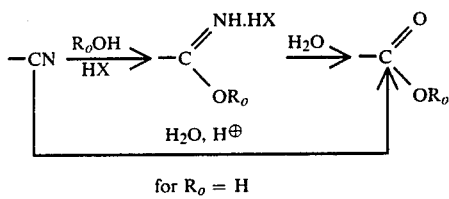

for $R_o$ = H

The stilbene compounds of the formula (1) can be used for producing known optical brighteners of the 4,4'-disubstituted stilbene series, for example those of the U.S. patent application No. U.S. Pat. No. 4,108,887. There are obtained by treatment with bases, with the removal of hydrogen halide, the α,β-unsaturated compounds of the formula

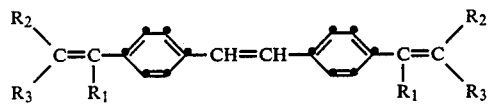

wherein $R_1$, $R_2$ and $R_3$ have the meanings defined in the foregoing.

The bases used are for example hydroxides or carbonates of alkali metals or alkaline-earth metals, preferably tertiary amines, such as trialkylamines, or pyridines. By the use of tertiary amines in an anhydrous medium, a possible transformation of the ester or nitrile groups can be avoided. If on the other hand there are used bases such as alkali metal hydroxides, ammonia or primary or secondary amines for the removal of hydrogen halide, the α,β-unsaturated dicarboxylic acids or amides thereof are obtained.

Except where otherwise stated in the following Examples, which further illustrate the invention without the scope thereof being limited to them, 'parts' are parts by weight and percentages are percent by weight. Melting points and boiling points are uncorrected, except where otherwise stated.

EXAMPLE 1

21 g of 4,4'-diaminostilbene are dissolved in a mixture of 56 ml of glacial acetic acid, 50 ml of conc. hydrochloric acid and 6 ml of water. The reaction mixture is cooled to 0° C. and, within 20 minutes, a solution of 15.2 g of sodium nitrite in 30 ml of water is added, in the course of which the temperature is not to exceed 5° C. The solution is subsequently filtered through glass frit. 31.9 g of acrylonitrile are placed into 24 ml of methyl ethyl ketone, and the whole is cooled to 10° C. Within a period of one hour, there are simultaneously added dropwise the solution of the diazonium salt and a solution of 1.5 g of copper(I) chloride in 15 ml of concentrated hydrochloric acid. The temperature in the reaction mixture is kept at 10°-20° C. by external cooling. After the evolution of nitrogen has finished, the precipitate is filtered off and washed neutral with water. The brown crystalline crude product (30.6 g; m.p. 120°-121° C.) is repeatedly boiled up in about 1 liter of ligroin, and the ligroin phase is decanted, the yellowish-white crystalline product crystallising out from the ligroin solution. There are thus obtained 18.3 g of the compound of the formula

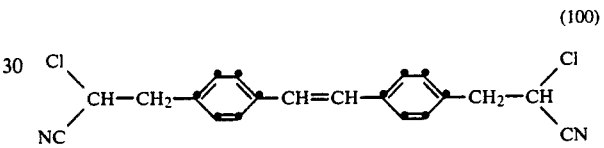
(100)

in the form of a crystalline product, m.p. 128°-132° C.

If there is used, instead of acrylonitrile, the corresponding amount of methyl vinyl sulfone, the addition of methyl ethyl ketone as solvent being dispensed with, there is obtained the compound of the formula

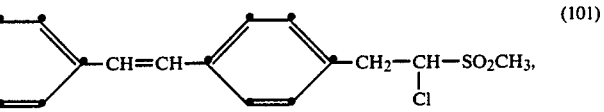
(101)

m.p. 268°-272° C. (after recrystallisation from ethylene glycol monomethyl ether).

The compounds of the formulae (102) and (103) are obtained in a similar manner from acrylic acid ethyl ester or acrylic acid.

EXAMPLE 2

To a solution of 3.55 g of the crude product of the formula (100) in 40 ml of methylene chloride are added 15 ml of anhydrous ethanol, and hydrochloric acid gas is fed in at 0° C., with stirring, until saturation is reached. After the reaction mixture has been allowed to stand for 16 hours at room temperature, it is evaporated to dryness at room temperature in vacuo, and the residue is stirred up in 40 ml of methylene chloride. The insoluble imino ether hydrochloride is filtered off under suction; it is then washed with methylene chloride and briefly dried at room temperature in vacuo (2.1 g). It is subsequently stirred up in a mixture of 10 ml of water and 10 ml of ethanol for 30 minutes at room temperature. The reaction product is filtered off, repeatedly washed with water and dried at 50° C. in vacuo. The yield is 1.3 g of the compound of the formula

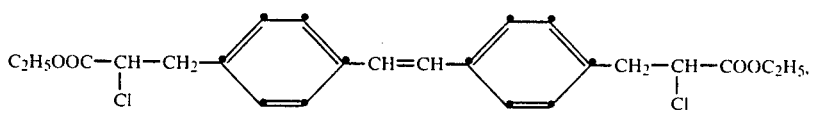

m.p. 95°–97° C. after recrystallisation from isopropanol and cyclohexane.

EXAMPLE 3

1.8 g of the crude product of the formula (100) are refluxed in 12 ml of formic acid and 8 ml of concentrated hydrochloric acid for 2 hours. After the starting product has gone into solution, the reaction product precipitates. This is filtered off with suction at room temperature, repeatedly washed with water and dried at 100° C. in vacuo. There are thus obtained 1.65 g of the compound of the formula

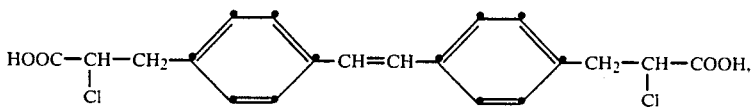

m.p. 204°–211° C., after recrystallisation from chlorobenzene.

EXAMPLE 4

6 g of the compound of the formula (100) are dissolved, with stirring, in 50 ml of dimethylformamide at room temperature. After the addition of 6.2 ml of triethylamine, the mixture is heated to 75° C., and stirred for 5 hours at this temperature. To the formed crude suspension are added 200 ml of methanol, and the whole is allowed to cool; the product which crystallises out is then filtered off under suction, washed with methanol and dried in vacuo. There are thus obtained 3.3 g of the optical brightener of the formula

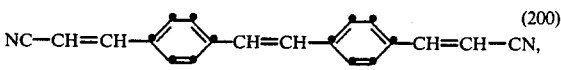

having a melting point of 192°–195° C.

There is obtained in an analogous manner, from the diethyl ester of the formula (102), the optical brightener of the formula

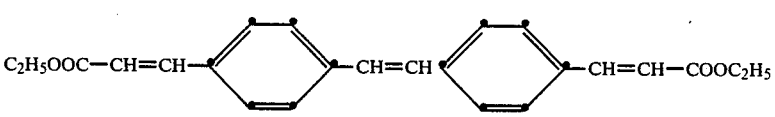

having a melting point of 200° C.

When the diethyl ester of the formula (102) or the dicarboxylic acid of the formula (103) is heated with excess, aqueous alcoholic sodium hydroxide solution at the reflux temperature, there is obtained, after acidification, the compound of the formula

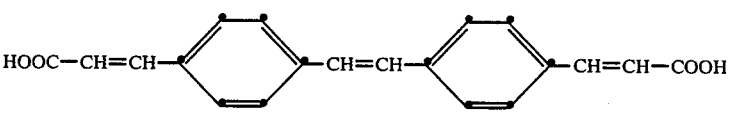

having a melting point of >300° C.

What is claimed is:

1. A stilbene derivative of the formula

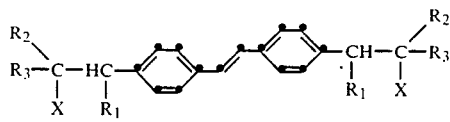

wherein

X is chlorine or bromine, $R_1$ is hydrogen, carboxyl, cyano, $C_1$–$C_6$-alkyl or a non-chromophorically esterified carboxyl group selected from the group consisting of carboxylic acid alkyl esters, where the alkyl moiety is unsubstituted or substituted by hydroxyl, alkoxy, alkoxyalkoxy, hydroxyalkoxy, or alkoxycarbonyl, and carboxylic acid alkenyl ester groups, where the alkenyl moiety is unsubstituted or substituted by alkoxy, hydroxyalkoxy or alkoxycarbonyl, and $R_2$ and $R_3$ independently of one another are each hydrogen, unsubstituted or non-chromophorically substituted $C_1$–$C_6$-alkyl or $C_3$–$C_4$-alkenyl, said non-chromophoric substituents being selected from the group consisting of alkoxy, hydroxyalkoxy or alkoxycarbonyl, or a non-chromophoric substituent of the 2nd order selected from the group consisting of cyano, carbonamido, carboxyl, carboxylic acid alkyl ester groups, wherein the alkyl moiety is unsubstituted or substituted by hydroxyl, alkoxy, alkoxyalkoxy or hydroxyalkoxy, and alkyl-, phenyl- and benzylsulfonyl groups, wherein the alkyl moiety is unsubstituted or substituted by alkoxy or alkoxyalkoxy.

2. A stilbene derivative according to claim 1, wherein $R_1$ is hydrogen, $C_1$–$C_4$-alkyl or COOR, in which R is $C_1$–$C_4$-alkyl or $C_3$–$C_4$-alkenyl, $R_2$ is hydrogen, $C_1$–$C_4$-alkyl, $C_1$–$C_4$-alkyl substituted by $C_1$–$C_4$-alkoxy or $C_1$–$C_4$-alkoxycarbonyl, or is $C_3$–$C_4$-alkenyl, cyano, —COOR$_o$, in which R$_o$ is hydrogen, $C_1$–$C_4$-alkyl, hydroxy-$C_2$–$C_4$-alkyl, $C_1$–$C_4$-alkoxy-$C_2$–$C_4$-alkyl, $C_1$–$C_4$-alkoxy-$C_2$–$C_6$-alkoxy-$C_2$–$C_4$-alkyl or $C_2$–$C_6$-hydroxyalkoxy-$C_2$–$C_4$-alkyl, or $SO_2R_x$, in which $R_x$ is $C_1$–$C_4$-alkyl, $C_1$–$C_4$-alkoxy-$C_2$–$C_4$-alkyl, $C_1$–$C_4$-alkoxy-$C_2$–$C_4$-alkoxy-$C_2$–$C_4$-alkyl, phenyl or benzyl, and $R_3$ is hydrogen, $C_1$–$C_4$-alkyl, or $C_1$–$C_4$-alkyl substituted by $C_1$–$C_4$-alkoxy or $C_1$–$C_4$-alkoxycarbonyl.

3. A stilbene derivative according to claim 2, wherein
X is chlorine,
$R_1$ is hydrogen or $C_1$–$C_2$-alkyl,
$R_2$ is $C_3$–$C_4$-alkenyl, cyano or —$COOR_o$ or —$SO_2R_x$, in which $R_o$ is hydrogen or $C_1$–$C_4$-alkyl and $R_x$ is $C_1$–$C_4$-alkyl, and
$R_3$ is hydrogen or $C_1$–$C_4$-alkyl.

4. A stilbene derivative according to claim 3, wherein
$R_1$ is hydrogen,
$R_2$ is cyano or —$COOR_o$ or —$SO_2R_x$, in which $R_o$ is hydrogen, methyl or ethyl, and $R_x$ is methyl or ethyl, and
$R_3$ is hydrogen.

5. A stilbene derivative according to claim 4, wherein $R_1$ and $R_3$ are hydrogen, and $R_2$ is cyano.

* * * * *